United States Patent [19]

Jourquin et al.

[11] 4,191,815
[45] Mar. 4, 1980

[54] HYDROPHILE POLYURETHANE FOAM, PROCESS FOR PREPARING SAID FOAM AND HYDROPHILE PRODUCT BASED ON SAID FOAM

[75] Inventors: Lucien Jourquin, Wetteren; Eddie Du Prez, St-Maria-Oudenhove, both of Belgium

[73] Assignee: s.a. PRB, Brussels, Belgium

[21] Appl. No.: 776,681

[22] Filed: Mar. 11, 1977

[30] Foreign Application Priority Data

Mar. 12, 1976 [LU] Luxembourg .............................. 74539

[51] Int. Cl.$^2$ ...................... C08G 18/14; C08G 18/20; B32B 27/40
[52] U.S. Cl. ........................................ 521/51; 428/315; 521/51; 521/121; 521/125; 521/129; 521/905
[58] Field of Search .................. 260/2.5 AD, 2.5 AT, 260/2.5 AB, 2.5 AC; 521/51, 121, 125, 129, 905

[56] References Cited

U.S. PATENT DOCUMENTS

| | | | |
|---|---|---|---|
| 3,422,036 | 1/1969 | Ellegast et al. | 260/2.5 AB |
| 3,476,933 | 11/1969 | Mendelsohn | 260/2.5 AC |
| 3,645,924 | 2/1972 | Fogiel | 260/2.5 AC |
| 3,769,244 | 10/1973 | Hashimoto et al. | 260/77.5 AC |
| 3,799,898 | 3/1974 | Lamplugh et al. | 260/2.5 AD |
| 3,814,707 | 6/1974 | Mueller et al. | 260/2.5 AK |
| 3,861,993 | 1/1975 | Guthrie | 260/2.5 AD |
| 3,874,964 | 4/1975 | Cogliano et al. | 260/2.5 AD |
| 3,953,406 | 4/1976 | Marsh | 260/2.5 AD |
| 3,975,350 | 8/1976 | Hudgin et al. | 260/2.5 AD |
| 3,993,608 | 11/1976 | Wells | 260/2.5 AW |
| 4,006,124 | 1/1977 | Welts et al. | 260/2.5 AW |
| 4,008,189 | 2/1977 | Leuwen et al. | 260/2.5 AD |
| 4,013,701 | 3/1977 | Jabs et al. | 260/2.5 AD |
| 4,025,466 | 5/1977 | Jourquin et al. | 260/2.5 AC |

FOREIGN PATENT DOCUMENTS 68552 6/1975 Luxembourg .

OTHER PUBLICATIONS

Analytical Chemistry, vol. 49, No. 12, Oct. 1977, 1676–1680.
Journ. Elastoplastics, vol. 3, Jan. 1971, p. 28.
Mumford et al., Chemical Characterization of Polyurethane Foams, Univ. of Utah (no data).
Mahoney et al., Environmental Sci. & Techn., vol. 8, No. 2, Feb. 1974, pp. 135–139.

*Primary Examiner*—H. S. Cockeram

*Attorney, Agent, or Firm*—Sughrue, Rothwell, Mion, Zinn and Macpeak

[57] ABSTRACT

A hydrophile polyurethane foam prepared from a hydrophile polyol, a polyisocyanate in which NCO groups are not directly bonded to an aromatic ring, a surface active agent, a swelling agent and a catalyst comprising:

(A) at least one compound selected from the group consisting of:
(1) diazabicyclo-alkenes of formula:

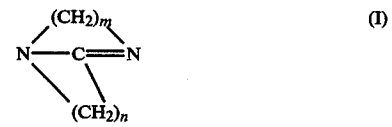

(2) substituted guanidines and salts of formula:

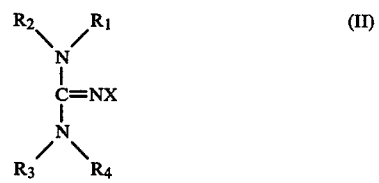

(3) substituted biguanidines of formula:

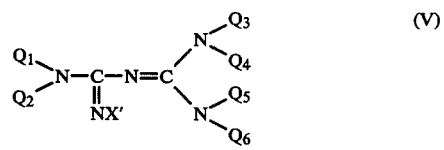

(4) substituted biguanidines of formula:

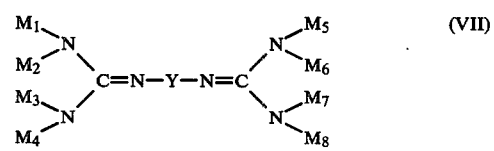

wherein the substituents can have different meanings, and
(B) at least an alkali metal or alkaline earth metal salt of organic acids having a dissociation constant $K_a < 10^{-1}$.

2 Claims, No Drawings

HYDROPHILE POLYURETHANE FOAM, PROCESS FOR PREPARING SAID FOAM AND HYDROPHILE PRODUCT BASED ON SAID FOAM

This invention relates to a hydrophile polyurethane foam prepared from a hydrophile polyol, a polyisocyanate, a surface-active agent, a catalyst and a swelling agent.

The heretofore hydrophile polyurethane foams are obtained from aromatic polyisocyanate, more particularly from toluenediisocyanate, known as "TDI".

It has been found that this kind of polyurethane foam forms, by hydrolysis of urethane bindings, aromatic amines, particularly toluene diamine, which are known as carcinogenic products.

This is a very important drawback for products of medical and hygienic use, such as sanitary towels, dressings and swaddling clothes, so that said polyurethane foams are not suitable for these specific applications. Thus, for example, sanitary towels made of said foams have been prohibited in the United States of America.

The object of this invention is to remedy this drawback and to provide a hydrophile polyurethane foam the adsorption properties of which are at least equal to those of known hydrophile foams.

To this end, the hydrophile polyurethane foam according to the invention is prepared from a polyisocyanate the NCO groups of which are not directly bonded to an aromatic ring.

Advantageously, said polyisocyanate is a polyisocyanate selected from the group comprising 2.4' (4.4')-methylene-bis (cyclohexylisocyanate), 3-isocyanatomethyl-3.5.5-trimethylcyclohexylisocyanate, 2.4.4-trimethyl hexamethylene diisocyanate, xylylene diisocyanate and hexamethylene diisocyanate.

According to a particular embodiment, the catalyst forming a part of the polyurethane foam composition according to the invention comprises:

(A) at least one compound selected from the group comprising:

(1) diazabicycloalkenes of formula:

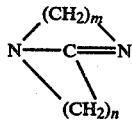

wherein m varies from 3 to 7 and n from 2 to 4, and salts thereof with organic acids the dissociation constant of which $Ka \leq 10^{-2}$, (2) substituted guanidines and salts thereof of formula:

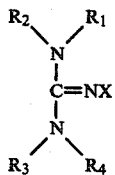

wherein $R_1$, $R_2$, $R_3$ and $R_4$ independently represent a $C_1$-$C_4$ alkyl radical, a $C_1$-$C_4$ alkyl radical substituted by a $C_1$-$C_4$ alkoxy radical, or a heterocyclic $C_5$-$C_7$ radical comprising at most two atoms from the group comprising sulfur and oxygen, $R_1$ and $R_2$ and/or $R_3$ and $R_4$ may form with adjacent nitrogen a heterocyclic $C_5$-$C_7$ ring containing at most a sulfur or oxygen atom, X represents hydrogen, phenyl, a phenyl group substituted by one or more $C_1$-$C_4$ alkoxy radicals, $C_1$-$C_{12}$ alkyl radicals or halogens, or represents a radical of formula:

wherein $R_5$, $R_6$ and $R_7$ independently represent hydrogen, a $C_1$-$C_4$ alkyl radical or a $C_1$-$C_4$ alkyl radical substituted by phenyl, substituted phenyl, $C_1$-$C_4$ alkoxy, $C_6$-$C_{15}$ aryloxy, nitrile, carbalkoxy, $R_7$ may represent a $C_5$-$C_{18}$ alkyl radical, a substituted phenyl radical or a $C_1$-$C_4$ alkoxy radical or also one or two of the groups $R_5$-$R_6$, $R_5$-$R_7$ and $R_6$-$R_7$ can form a cyclic ring of carbon atoms with not more than one nitrogen, sulfur or oxygen atom, X may also represent a radical of formula:

wherein z is an integer from 2 to 12, R' and R" represent hydrogen or a $C_1$-$C_4$ alkyl radical, R''' and R'''' represent a $C_1$-$C_4$ alkyl radical or form with adjacent nitrogen a $C_5$-$C_6$ cycloalkyl radical, as well as addition salts of said guanidines, and addition salts of guanidines wherein at least one of $R_1$, $R_2$, $R_3$ and $R_4$ is hydrogen, with an acid having a disociation constant $Ka \leq 10^{-3}$; (3) substituted biguanidines of formula:

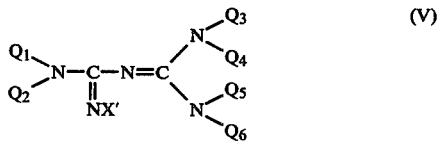

wherein $Q_1$ to $Q_6$ independently represent a $C_1$-$C_4$ alkyl or a $C_3$-$C_4$ cycloalkyl radical, and X' is hydrogen or a carbamoyl radical of formula:

in which Z is a monovalent radical remaining after elimination of an isocyanate group from the above mentioned polyisocyanate, $Q_1$ to $Q_6$, X' and Z may optionally be substituted by chlorine, bromine or alkoxy ($C_1$ or $C_2$); (4) substituted biguanidines of formula:

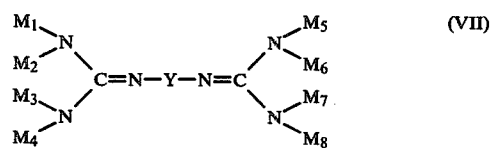

wherein $M_1$ to $M_8$ independently represent a $C_1$-$C_4$ alkyl radical, y represents a group:

$$\begin{matrix} M_9 \\ | \\ {+C+}_\alpha \\ | \\ M_{10} \end{matrix} \qquad (VIII)$$

wherein $M_9$ and $M_{10}$ represent hydrogen or a $C_1$–$C_4$ alkyl radical, and $\alpha$ is an integer from 3 to 12, or also represents a divalent cyclohexyl radical or a divalent isophorone radical; and (B) at least an alkali metal or alkaline earth metal salt of organic acids having a dissociation constant $Ka < 10^{-1}$, preferably $Ka < 10^{-2}$.

This invention also concerns a process for preparing said foam, comprising reaction of a hydrophile polyol, a polyisocyanate wherein NCO groups are not directly bonded to an aromatic ring, a foam stabilizer, a swelling agent and a suitable catalyst, more particularly a catalyst formed by combining at least two of the above-mentioned compounds.

The invention also concerns hydrophile products, more particularly sanitary towels, dressings and swaddling-clothes, containing hydrophile polyurethanes foam according to the invention.

Other details and features of the invention will become apparent from the description given hereinafter of some particular embodiments of the invention.

The present invention consists of providing a flexible polyurethane foam which is more particularly applicable in the medical and hygienic field due to its quite specific properties.

This is a polyurethane foam which is prepared by association of a hydrophile polyol and a polyisocyanate the NCO groups of which are not directly bonded to an aromatic ring. This foam also comprises a swelling agent, a surface active agent, such as a foam stabilizer, and a catalyst. Due to the nature of polyisocyanates used, the latter do not form, due to possible hydrolysis, aromatic amines which are known as being carcinogenic products.

The nature of each constituent of the polyurethane foam according to the invention may be quite varying.

Hereinafter an outline of various polyols, polyisocyanates, catalysts, swelling agents and foam stabilizers susceptible to be used in the polyurethane foam composition according to the invention is given.

Hydrophile polyol can possibly be formed of a mixture of various types of polyols at least one of which must have hydrophile properties. Said hydrophile polyol may be of the polyether or polyester kind.

Polyether polyols are generally product obtained from polyaddition of epoxides, particularly ethylene and/or propylene oxides, with low molecular weight polyfunctional polyols, polyamines or alkanolamines, said products being known in the manufacture of conventional flexible polyurethane foams and having been described in the literature, such as in Canadian Pat. No. 918,675 of du Pont de Nemours, U.S. Pat. No. 3,778,390 of Proctor and Gamble, and German Pat. No. 2,354,952 of Imperial Chemical Industries.

In order to give the foam desired hydrophile properties, the content of ethylene oxide groups with respect to the sum of ethylene and propylene oxide groups must be high enough, hydrophile properties being a direct function of the percentage of ethylene oxide groups in the polyol or mixture of polyols. Minimum percentage of ethylene oxide with respect to the sum of ethylene and propylene oxide groups, in order to obtain high enough hydrophile properties must be of at least 5%, preferably of at least 15%. Hydrophile polyols can be obtained according to various ways, which are as follows:

by association of conventional polyether polyols having a relatively low or even null content of ethylene oxide groups with polyols rich in ethylene oxide groups, such as polyoxyethylene glycols and commercial polyols known under the following designations: Pluronics and Tetronics of BASF-Wyandotte, Lupranol 1180 of BASF Kuhlman (previously known as Pluracol MK 93), Bermadol 87 of Berol-Kemi;

by one-step synthesis of polyethylene epoxide-polypropylene oxide copolymers rich in ethylene oxide units;

by combination of these kinds of polyols.

Such polyols and polyol mixtures are particularly described in Belgian Pat. No. 768,054 of Nauer.

Some typical examples of known commercial polyols are:

SA 1421 (Dow Chemical Cy)

X601, X603, X607 (Olin)

Pluracol 395 and 396 (Wyandotte)

PR 7015, PR 7020, PR 7048 (Wyandotte)

Napiol 444 (Sodethane)

Desmophene DD 3061 (Bayer)

The overall hydroxyl number of the polyol mixture is of about 20 to 80, preferably of about 30 to 60 for manufacture of flexible foam.

Polyester polyols are condensation products having terminal hydroxy groups, obtained by esterification of polycarboxy acids with excess of polyalcohols, optionally in the presence of polyamines or alkanolamines giving rise to amide groupings in the chain, polyalcohols, polyamines, and alkanolamines having low molecular weight polyfunctional bonds, such as known in the usual manufacture of polyurethane foam and described in the literature, particularly in French Pat. No. 2,077,383 and Canadian Pat. No. 918,675 of du Pont de Nemours, in German Pat. No. 2,354,952 of Imperial Chemical Industries, in Canadian Pat. No. 822,188 of Mobay, or also polyester polyols such as obtained by open chain polymerization of caprolactone.

Polyester polyols must however be "modified" so as to obtain high enough hydrophile properties. This is a well known technique which does not form a part of the present patent application so that it is not described hereinafter.

As example of commercial hydrophile polyester polyols, products known under the designations "Fomrez 45" of Witco and "Versuchsproducten PU 3092 and PU 3101" of Bayer may be mentioned.

The hydrophile polyurethane foam according to the invention is obtained from polyisocyanate the NCO groups of which are not directly bonded to an aromatic ring.

Said polyisocyanates can optionally be as prepolymers by modification with low molecular weight polyalcohols, polyamines or alkanolamines, or can form prepolymers with polyols of the polyether or polyester kind, such as hereinbefore described.

Examples of said polyisocyanates are: ethylenediisocyanate, propylene-1,2-diisocyanate, ethylidene-diisocyanate, hexamethylene-diisocyanate, 2,2,4-trimethyl-hexamethylene-diisocyanate, cyclohexylene-1,2-diisocyanate, 3-isocyanatomethyle-3,5,5-trimethyl-cyclohexylisocyanate, m and p-xylylene-diisocyanate, 4,4-methylene-bis(cyclohexylisocyanate), 2(4)4'-methylene-bis(cyclohexyl-isocyanate), 2-methyl-1,3-cyclohexylene-diisocyanate, bis(2-isocyanatoethyl)carbonate, and the like.

French Pat. No. 2,077,388 and Canadian Pat. No. 918,675 also mention polyisocyanates which can be suitable for preparing the polyurethane foam according to the invention.

Amongst preferred polyisocyanates, hexamethylene-diisocyanate, 2.4.4-trimethylhexamethylene-diisocyanate, 2,4'(4,4')-methylene-bis(cyclohexylisocyanate), 3-isocyanatomethyl-3,5,5-trimethylcyclohexylisocyanate, and xylylene-diisocyanate may be cited.

As already mentioned hereinbefore, prepolymer derivatives of polyisocyanates obtained by reaction with a lower than stoichiometrical amount of polyols of the polyether or polyester type or of low molecular weight compounds which are at least difunctional, such as low molecular weight initiators or polyols, polyamines or alkanolamines, such as described for example in already mentioned Canadian patent 822,188, may also be contemplated.

In case of prepolymers, the content of NCO groups must be of at least 5%.

The isocyanate index may vary between 70 and 120.

Catalysts used are preferably a synergistic combination of at least two kinds of compounds forming part of the Luxemburg Pat. No. 68,552.

This may be for example a catalytic combination comprising:

(A) at least one compound selected from the group comprising:

(1) diazabicycloalkenes of formula:

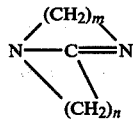
(I)

wherein m varies from 3 to 7 and n from 2 to 4, and salts thereof with organic acids the dissociation constant of which $Ka \leq 10^{-2}$, (2) substituted guanidines and salts thereof of formula:

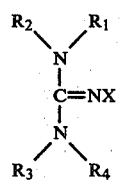
(II)

wherein $R_1$, $R_2$, $R_3$ and $R_4$ independently represent a $C_1$-$C_4$ alkyl radical, a $C_1$-$C_4$ alkyl radical substituted by a $C_1$-$C_4$ alkoxy radical, or a heterocyclic $C_5$-$C_7$ radical comprising at most two atoms from the group comprising sulfur and oxygen, $R_1$ and $R_2$ and/or $R_3$ and $R_4$ may form with adjacent nitrogen a heterocyclic $C_5$-$C_7$ ring containing at most a sulfur or oxygen atom, X represents hydrogen, phenyl, a phenyl group substituted by one or more $C_1$-$C_4$ alkoxy radicals, $C_1$-$C_{12}$ alkyl radicals or halogens, or represents a radical of formula:

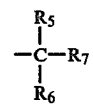
(III)

wherein $R_5$, $R_6$ and $R_7$ independenty represent hydrogen, a $C_1$-$C_4$ alkyl radical or a $C_1$-$C_4$ alkyl radical substituted by phenyl, substituted phenyl, $C_1$-$C_4$ alkoxy, $C_6$-$C_{15}$ aryloxy, nitrile, carbalkoxy, $R_7$ may represent a $C_5$-$C_{18}$ alkyl radical, a substituted phenyl radical or a $C_1$-$C_4$ alkoxy radical or also one or two of the groups $R_5$-$R_6$, $R_5$-$R_7$ and $R_6$-$R_7$ can form a cyclic ring of carbon atoms with not more than one nitrogen, sulfur or oxygen atom, X may also represent a radical of formula:

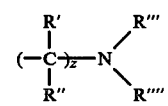
(IV)

wherein z is an integer from 2 to 12, R' and R" represent hydrogen or a $C_1$-$C_4$ alkyl radical, R''' and R'''' represent a $C_1$-$C_4$ alkyl radical or form with adjacent nitrogen a $C_5$-$C_6$ cycloalkyl radical, as well as addition salts of said guanidines, and addition salts of guanidines wherein at least one of $R_1$, $R_2$, $R_3$ and $R_4$ is hydrogen, with an acid having a dissociation constant $Ka \leq 10^{-3}$; (3) substituted biguanidines of formula:

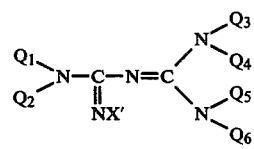
(V)

wherein $Q_1$ to $Q_6$ independently represent a $C_1$-$C_4$ alkyl or a $C_3$-$C_4$ cycloalkyl radical, and X' is hydrogen or a carbamoyl radical of formula:

(VI)

in which Z is a monovalent radical remaining after elimination of an isocyanate group from the above mentioned polyisocyanate, $Q_1$ to $Q_6$, X' and Z may optionally be substituted by chlorine, bromine or alkoxy ($C_1$ or $C_2$); (4) substituted biguanidines of formula:

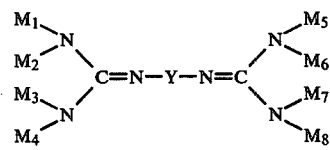
(VII)

wherein $M_1$ to $M_8$ independently represent a $C_1$-$C_4$ alkyl radical, y represents a group:

(VIII)

wherein $M_9$ and $M_{10}$ represent hydrogen or a $C_1$–$C_4$ alkyl radical, and $a$ is an integer from 3 to 12, or also represents a divalent cyclohexyl radical or a divalent isophorone radical; and (B) at least an alkali metal or alkaline earth metal salt of organic acids having a dissociation constant $Ka < 10^{-1}$, preferably $Ka < 10^{-2}$.

It is important to mention that most of the compounds such as hereinbefore mentioned are already known as independent catalysts in the preparation of aromatic polyisocyanate-based polyurethane foam, namely a polyisocyanate in which said NCO groups are directly bonded to an aromatic ring.

It is known that if said compounds are separately used as catalysts in the preparation of polyurethane foams from a polyurethane cyanate, the NCO groups of which are not directly bonded to an aromatic ring, important reaction problems are raised industrially, due to low reactivity of such polyisocyanates and for example, it is not possible to use the so-called "one-shot" technique in such a case.

Although some specific catalytic combinations enjoy a preference of prime importance, one of the main objects of the invention is the selection of one or more compounds comprised in a group (A) of compounds such as defined in the literature as a class of independent products used in the preparation of polyurethane foam in combination with one or more compounds forming part of one or two other groups (B) of compounds such as defined in the literature as another class of independent products also used in the preparation of polyurethane foam.

Prima facie, some technical equivalency may be admitted between the various compounds of a same group with regard to the preparation of the catalytic combination according to the invention.

Amines of group (A) can be subdivided into different subgroups most of them are defined as such in the literature.

These subgroups are:
(a) diazabicycloalkenes and salts thereof, such as for example defined in French Pat. No. 1,542,058 and Canadian Pat. No. 881,617;
(b) guanidines, substituted or not, and salts thereof, for example such as described in French Pat. No. 2,077,388, Canadian Pat. No. 918,675, German Pat. No. 1,950,275 and U.S. Pat. No. 3,621,020;
(c) biguanidines;
(d) isobiguanidines such as described for example in U.S. Pat. No. 3,621,020.

Amongst amino compounds such as hereinbefore mentioned, the following compounds are of particular interest:
- 1,5-diazabicyclo (4,3,0) nonene-5,
- 1,8-diazabicyclo (5,4,0) undecene-7,
- 1,8-diazabicyclo (5,3,0) decene-7,
- 1,5-diazabicyclo (4,4,0) decene-5,
- 1,4-diazabicyclo (3,3,0) octene-4
- addition salts of said diazabicycloalkenes with mono- or dicarboxylic acids, carbonic acid, or phenols,
substituted guanidines having the formula:

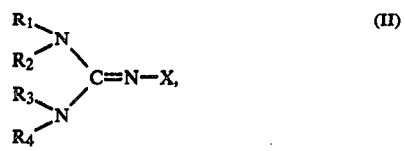

wherein X is hydrogen, a methyl, cyclohexyl, decyl, dodecyl, alkylphenyl ($C_1$–$C_4$) radical or a radical of the formula —$(CH_2)_z N(R'''R'''''')$ in which z is equal to 2 or 3 and $R'''$ and $R''''''$ are identical or different and are an alkyl ($C_1$–$C_4$) radical, $R_1$ to $R_4$ representing a methyl radical, as well as addition salts of said guanidines, and addition salts of guanidines of formula (II), in which moreover at least $R_1$ and $R_2$ are hydrogen, with carbonic acid and phenol,
- 1.1.4.4.5.5-hexamethylisobiguanidine and substituted biguanidines of the formula:

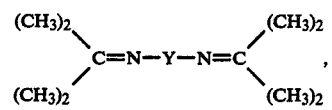

in which Y is a divalent alkylene ($C_6$–$C_{12}$) radical.

As hereinbefore mentioned, said amino compounds must always be used in combination with at least one metal salt, metal alcoholate and/or metal phenolate.

A preference is given to compounds of the group comprised of sodium and potassium salts of oleic acid, 2.3-methylbenzoic acid, adipic acid, 2.4-dichlorobenzoic acid, benzoic acid, β-chloroacetic acid, chloro-and bromobenzoic acid, salicylic acid, acetic acid, formic acid, and of sodium and potassium phenolate and methylate.

These catalysts can optionally be completed with catalysts, which are known in the manufacture of polyurethane foam from traditional aromatic polyisocyanates, such as tertiary amines and organo-metal compounds; such catalysts have for example been described in U.S. Pat. No. 3,799,898.

With regard to swelling agents used, the latter comprise water in a ratio of 0.5 to 7 parts by weight to 100 parts by weight of polyol, preferably 1 to 5 parts by weight.

This water, which is a chemical swelling agent causing $CO_2$ to be formed, can optionally be completed with a physical swelling agent, which generally is an inert organic solvent which evaporates and thus creates a gas inside the foam. The most typical agents of this kind are trifluoromethane and methylene chloride. The amount of such a physical swelling agent may generally be at most 30 parts by weight, preferably at most 15 parts by weight to 100 parts by weight of polyol.

Surface active agents are generally those such as usually used in the manufacture processes of polyurethane foam and are for example described in U.S. Pat. Nos. 3,778,390 and 3,799,898 and French Pat. No. 2,077,388.

Said surface active agents may be of different kinds. For example, they may be silicones, such as polydimethylsiloxane-polyoxyalkylene copolymers, non ionic surface active agents, such as polyglycol ethers of alkylphenols, polyglycol ethers of fatty acids, alkylolamides of fatty acids, polyolethylated vegetable oils, oxyethylated amines and polyamines, polyoxyethylated monoesters of sorbitol and fatty acids, or also anionic surface active agents, such as alkylbenzene sulfonic acids, alkylbenzene sulfonates (as sodium salts), sodium sulfates of fatty alcohols, sodium sulfates of polyglycol ethers of fatty acids, phosphates of polyglycol ethers, sulfonated or sulfated polyoxyethylene fatty acid adducts.

The amount of surface active agents are generally 0.1 to 30 parts by weight to 100 parts by weight of polyol, provided that said agent does not comprise silicone, preferably 0.5 to 10 parts by weight. In the case the surface active agents would be formed of silicone, the content thereof would generally be about 0.1 to 10 parts by weight, preferably 0.2 to 3 parts by weight to 100 parts by weight of polyol.

It is also to be noted that according to the invention hydrophile properties of polyurethane foam can be improved by selection of surface active agents. Thus use of surface active agents comprising polyethylene oxide groups can have a very favourable influence on hydrophile properties of the polyurethane foam so obtained.

It is however to be noted that the surface active agent which is generally a foam stabilizer, usually comprises a silicone-based product so as to ensure an optimum stabilization of cells in the foam in process to be formed.

The flexible hydrophile polyurethane foam such as hereinbefore described according to the invention can be obtained by traditional methods which are one-shot process, prepolymer process and quasi-prepolymer process. These processes are for example described in U.S. Pat. No. 3,778,390, column 4, lines 41–57.

Typical preparation examples of some specific polyurethane foams according to the invention are given hereinafter.

Said examples have been grouped in the following Tables. The values given in the columns are parts by weight. The term "idem" means that data or conditions are the same as in the preceding Example.

| Number of example | 1 | 2 | 3 | 4 | 5 | 6 |
| --- | --- | --- | --- | --- | --- | --- |
| 1. Ingredients | | | | | | |
| (a) polyol | SA 1421:70 D 3900:30 | idem | idem | idem | idem | idem |
| (b) isocyanate | Hylene W:66.3 | idem | idem | idem | idem | idem |
| NCO index | 100 | idem | idem | idem | idem | idem |
| (c) swelling agent | Water:4 | idem | idem | idem | idem | idem |
| (d) surface-active agent | L 520:1.5 | idem | idem | idem | idem | idem |
| (e) catayst | TMG:2 Sodium Benzoate:2 DBTL:0.5 | DBU:1 Sodium Acetate:2.5 | DBN:2 Potassium Acetate:1 Polycat 8:1 | Guanidine acetate 3 Sodium phenolate 1 | TMG:3 SO:1 | Dabco:2 Polycat 8:2 DBTL-1 |
| 2. Reaction characteristics | | | | | | |
| (a) RG | 35 | 37 | 37 | 34 | — | — |
| (b) CRT | 16 | 15 | 14 | 19 | — | — |
| (c) RT | 60 | 62 | 55 | 71 | — | — |
| (d) GT | 51 | 51 | 40 | 59 | — | — |
| 3. Hydrophile properties | | | | | | |
| (a) penetrability (dry) | 50 | 62 | 60 | 56 | — | — |
| penetrability (wet) | 10 | 15 | 10 | 16 | — | — |
| (b) capillarity | 0.9 | 1 | 0.9 | 1.1 | — | — |
| (c) absorption power | ×30 | ×30 | ×25 | ×35 | — | — |
| (d) swelling | 30 | 35 | 25 | 30 | — | — |

| Number of example | 7 | 8 | 9 | 10 | 11 | 12 | 13 |
| --- | --- | --- | --- | --- | --- | --- | --- |
| 1. Ingredients | | | | | | | |
| (a) polyol | DD 3061:100 | idem | idem | idem | idem | idem | idem |
| (b) isocyanate 50% IPPI 50% Hylene W | 50.4 | idem idem idem | idem idem idem | idem idem idem | idem idem idem | idem idem idem | idem idem idem |
| index NCO | 110 | idem | idem | idem | idem | idem | idem |
| (c) swelling agent | Water:3 Freon:7 | idem idem | idem idem | idem idem | idem idem | idem idem | idem idem |
| (d) surface-active agent | B 2370:1.3 | idem | idem | idem | idem | idem | idem |
| (e) catalyst | TMGDO:0.8 Sodiumpentachlorophenolate:1.5 | TMGC:1.5 Sodiumpropionate:1 | guanidine acetate:1.5 potassium oleate:2 | DBC-butyrate 4 Lithium acetate:1 | HOBG:1.5 Sodiumdichloroacetate:1. | DBU-phenolate:2 Disodium phthalate:2 | Sodium-acetate 3 Cat.Al.:0.5 So:1 |
| 2. Reaction characteristics | | | | | | | |
| (a) RG | 32 | 33 | 30 | 34 | 34 | 32 | — |
| (b) CRT | 19 | 21 | 18 | 19 | 22 | 18 | — |
| (c) RT | 67 | 72 | 65 | 81 | 75 | 80 | — |
| (d) GT | 50 | 55 | 51 | 64 | 59 | 65 | — |
| 3. Hydrophile properties | | | | | | | |
| (a) penetrability (dry) | 22 | 38 | 40 | 53 | 52 | 29 | — |
| penetrability (wet) | 5 | 3 | 9 | 9 | 6 | 10 | — |
| (b) capillarity | 1.5 | 1.7 | 1.3 | 2 | 1.6 | 1.6 | — |
| (c) absorption power | ×34 | ×40 | ×37 | ×39 | ×30 | ×37 | — |
| (d) swelling | 85 | 95 | 80 | 100 | 80 | 95 | — |

| Number of example | 14 | 15 | 16 | 17 |
| --- | --- | --- | --- | --- |

-continued

| 1. Ingredients | | | | |
|---|---|---|---|---|
| (a) polyol + (b) | Cl 3002 prepolymer + excess of IPDI - NCO %:15ˣ 100 parts Poly(ethylene oxide) glycol, MW600:15 IPDI:10 | idem id:14 idem | idem Lupranol 1180:30 idem | idem Lupranol 1180:20 idem |
| (c) swelling agent | Water:3 | idem | idem | idem |
| (d) surface-active agent | WM:3 | DC 200 - 200 cts | DD 3045:0.5 | M66-82:3 |
| (e) catalyst | TMG:1 Sodiumphenolate of β-naphtol:1 | PMG:0.8 Potassium m-cresolate:1 | HOBG:0.9 Disodium salicylate 2 | DBO oleate:2 Potassium acetate: 0.5 |
| 2. Reaction characteristics | | | | |
| (a) RG | 32 | 33 | 30 | 33 |
| (b) CRT | 9 | 13 | 10 | 10 |
| (c) RT | 53 | 65 | 51 | 70 |
| (d) GT | 40 | 52 | 33 | 55 |
| 3. Hydrophile properties | | | | |
| (a) penetrability (dry) | 44 | 68 | 50 | 46 |
| penetrability (wet) | 12 | 20 | 9 | 10 |
| (b) capillarity | 1.4 | 0.8 | 1.1 | 1.1 |
| (c) absorption power | ×37 | ×28 | ×35 | ×33 |
| (d) swelling | 25 | 15 | 35 | 30 |

| Number of example | 18 | 19 | 20 | 21 | 22 | 23 | 24 |
|---|---|---|---|---|---|---|---|
| 1. Ingredients | | | | | | | |
| (a) polyol | F 45:100 | idem | idem | idem | idem | dem | idem |
| (b) isocyanate | TMDI: | idem | idem | idem | idem | idem | idem |
| NCO index | 100 | idem | idem | idem | idem | idem | idem |
| (c) swelling agent | 3.5 | idem | idem | idem | idem | idem | idem |
| (d) surface-active agent | EM:2 TX:2 | A 381 A:1.5 | DC 193:1 | 1058:2 77/86:2 | B 2008:1.5 | L532:1.5 | L532:1.5 |
| (e) catalyst | DBC:1.5 Potassium acetate:0.5 | guanidine phenolate:1 Sodium acetate 1.5 | para-ethyl TMGP 2; potassium salt of p-chlorobenzoic acid:1 | TMGD:2 Potassium phenolate: 1 | guanidine carbonate:1 sodium methylate:1 | NEM:5 Dabco:1 SO:0.5 | Sodium acetate:5 DBTL:0.5 |
| 2. Reaction characteristics | | | | | | | |
| (a) RG | 36 | 33 | 33 | 37 | 35 | — | — |
| (b) CRT | 10 | 13 | 13 | 11 | 10 | — | — |
| (c) RT | 65 | 66 | 72 | 68 | 69 | — | — |
| (d) GT | 50 | 54 | 61 | 56 | 60 | — | — |
| 3. Hydrophile properties | | | | | | | |
| (a) penetrability (dry) | 34 | 56 | 65 | 31 | 48 | — | — |
| penetrability (wet) | 3 | 10 | 10 | 6 | 9 | — | — |
| (b) capillarity | 1.3 | 0.7 | 0.7 | 1.2 | 1.0 | — | — |
| (c) absorption power | ×35 | ×25 | ×23 | ×31 | ×28 | — | — |
| (d) swelling | 5 | 3 | 3 | 7 | 5 | — | — |

| Number of example | 25 | 26 | 27 | 28 |
|---|---|---|---|---|
| 1. Ingredients | | | | |
| (a) polyol | PU 3092:100 | idem | idem | idem |
| (b) isocyanate | XDI:40.2 | idem | idem | idem |
| NCO index | 90 | idem | idem | idem |
| (c) swelling agent | Water:3.5 MC:5 | idem idem | idem idem | idem idem |
| (d) Surface-active agent | L532:1 | Triton:X100:2 Tensaryl SB 55 P:2 | M66-82:3 | WM:2 SM:2 |
| (e) Catalyst | TMGDO-1 Dipotassium adipate 1 | DBU phenolate:1.5 Potassium phenolate of 2.4-dibromophenol:2 | DBN:1 Sodium laurate:3 | TMG:2 Na 2-ethyl-hexoate: 2 |
| 2. Reaction characteristics | | | | |
| (a) RG | 29 | 29 | 33 | 32 |
| (b) CRT | 16 | 20 | 15 | 17 |
| (c) RT | 63 | 77 | 68 | 57 |
| (d) GT | 48 | 68 | 51 | 42 |
| 3. Hydrophile properties | | | | |
| (a) penetrability (dry) | 38 | 24 | 50 | 32 |
| penetrability (wet) | 5 | 7 | 6 | 3 |
| (b) capillarity | 1.3 | 1.8 | 1.5 | 2 |
| (c) absorption power | ×27 | ×30 | ×32 | ×3 |
| (d) swelling | 5 | 6 | 3 | 7 |

-continued

| Number of example | 29 | 30 | 31 |
|---|---|---|---|
| 1. Ingredients | | | |
| (a) polyol | F 45:100 | idem | idem |
| (b) isocyanate | IPDI:53 | idem | idem |
| NCO index | 100 | idem | idem |
| (c) swelling agent | Water:3.5 | idem | idem |
| (d) catalyst | Metachloro TMGP:2 Sodium chloroacetate 1 | TMGN:1.5 Sodium formiate:1.5 | HMIB:1.5 Potassium salt of 2.4 dichlorobenzoic acid: 1 |
| (e) surface-active agent | L 532:1.5 | idem | idem |
| 2. Reaction characteristics | | | |
| (a) RG | 34 | 35 | 31 |
| (b) CRT | 12 | 12 | 10 |
| (c) RT | 64 | 70 | 68 |
| (d) GT | 55 | 61 | 60 |
| 3. Hydrophile properties | | | |
| (a) penetrability (dry) | 39 | 46 | 36 |
| penetrability (wet) | 8 | 10 | 10 |
| (b) capillarity | 1.1 | 1.2 | 1.1 |
| (c) absorption power | ×29 | ×31 | ×29 |
| (d) swelling | 4 | 3 | 3 |

Information on symbols and names used in the various Tables (1) Ingredients (a) Polyols SA 1421: hydrophile polyether polyol of Dow Chemical, containing a large number of oxyethylene groups and the hydrophyl number of which is about 33;

D 3900: Desmophene 3900 of Bayer, comprising active polyether triol having a hydroxyl number of about 35;

Lupranol 1180: known under the commercial name Eurane of BASF-Kuhlman and comprising a polyether triol having a high content of oxyethylene groups and a hydroxyl number of about 42;

DD 3061: hydrophile polyether known under the commercial name Desmophene TD 3061 of Bayer and comprising a large number of oxyethylene groups, the hydroxyl number being about 27;

F 45: known under the commercial name Fomrez 45 of Witco and comprising a special hydrophile polyester polyol, the hydroxy number of which being 50;

PU 3092: Test product of Bayer comprising a special hydrophile polyester polyol, the hydroxyl number of which being 50;

CP 3002: active polyether known under the designation Voranol CP 3002 of Dow Chemical with a hydroxyl number of about 55.

(b) Isocyanates

Hylene W: commercial name of a du Pont de Nemours product, comprising a stereoisomer of 4.4′-methylenebis (cyclohexylisocyanate) containing 32% of NCO groups;

IPDI: commercial name (Veba Chemie, Germany) of 3-isocyanatomethyl-3.5.5-trimethylcyclohexylisocyanate containing about 37.8% of NCO groups;

TMDI: 2.4.4-trimethyl hexamethylene diisocyanate containing 40% NCO groups;

XDT: commercial name of xylylene diisocyanate, comprised of a mixture of 70% meta-isomer and 30% para-isomer, said mixture having a content of NCO groups of 45%.

(c) Surface active agents

L532 and L520: commercial names of polysiloxane and polyoxyalkylene copolymers which are silicone surface active agents of Union Carbide;

B 2370 and B 2008: commercial names of polysiloxane and polyoxyalkylene copolymers which are surface active agents of Goldschmidt;

DC 193: commercial name of a polysiloxane-polyoxyalkylene copolymer, which is a silicone surface active agent of Dow Corning;

DD 3045: commercial name of a special tensio-active agent of Bayer;

DC 200,200cts: commercial name of silicone oil of polydimethyl siloxane of Dow Corning, the viscosity of which is 200 cts;

M 6682, A 381 A and 1058: organic surfaces active agents of Witco which do not contain any silicone;

77–86: sulfated or sulfonated fatty acid additive of ethylene oxide and propylene oxide of Witco;

WM,EM,TX and SM: commercial names of emulsifier surface active agents of Bayer, which do not contain any silicone;

Triton X 100: commercial name of an ethylene oxide-octylphenol adduct of Rohm and Haas;

Tensaryl SB 55 P: commercial name of alkylbenzene sulfate (sodium salt) of Tensia-Belgium.

(d) Catalysts

TMG: tetramethylguanidine;
TMGC: cylcohexyltetramethylguanidine
PMG: pentamethylguanidine
TMGD: n-decyltetramethylguanidine
TMGDO: n-dodecyltetramethylguanidine
DBU: 1.8-diazabicyclo(5.4.0)undecene-7
DBN: 1.5-diazabicyclo(4.3.0)nonene-5
DBC: 1.5-diazabicyclo(4.4.0)decene-5
DBO: 1.4-diazabicyclo(3.3.0)octene-4
DBTL: Sn dibutyldilaurate
SO: stannous octoate
"Cat.Al": commercial name of a mixture of 70% $(CH_3)_2N—(CH_2)_2—O—(CH_2)_2—N—(CH_3)_2$ and 30% dipropylene glycol of Union Carbide, "Polycat 8": commercial name of dimethylcycohexylamine of Abbott Chemicals
NEM: N-ethylmorpholine
Dabco: triethylene diamine (Houdry)
TMGN: dimethyl-aminoethyl-tetramethylguanidine
HMIB: 1.1.4.4.5.5-hexametylisobiguanidine
TMGP: phenyl-tetramethylguanidine
HOBG: hexamethylene-octamethyl-biguanidine (e) Swelling agents
water
freon: trichlorofluormethane
MC: methylene dichloride (2) Reaction characteristics (a) RG: foam density in kg/m$^3$
(b) CRT: cream time, in seconds
(c) RT: full rise time in seconds
(d) GT: gel time in seconds, which corresponds to the moment when elastic polyurethane thread can be drawn from the rising foam by means of an iron rod having been contacted with this foam.

(3) Hydrophile properties (a) Wet out : time in second which is necessary to allow a water drop of 1 cc, laid on a foam sample by means of a pipette to completely penetrate into the surface of this sample. This can be carried out on a dry sample or on a previously wetted and centrifuged sample (penetrability test).
(b) Wicking speed : this value corresponds to the height of water film in cm, rising into a foam sample of 10×2.5×1.27 cm, laid with one of its ends into a water container, from water surface after 3 minutes (in cm/ 3 min);
(c) Absorption power : this value corresponds to the weight increase of a foam sample of a known weight, fully water saturated and drained for 60 seconds, with respect to the weight of dry sample;
(d) Swelling : volume increase in % of a fully water saturated sample with respect to the original dry sample.

In Examples 1 to 6, the so-called "one-shot" technique was applied on different starting compositions which are only different with regard to the nature of the catalyst used, other ingredients being identical as well in the kind as in quantity.

All the ingredients, except isocyanate, were stirred together until a substantially homogeneous mixture was obtained. Then isocyanate was added and the whole was intensively stirred for about 10 seconds. The so obtained mixture was then poured into an open container wherein foam was free to form.

In Examples 1 to 4, a catalytic combination according to the invention was used, while by way of comparison, Examples 5 and 6 relate to use of a conventional catalytic combination.

It was found that for Examples 1 to 4, the various reaction steps of foam formation were in quite complete equilibrium and allowed a foam to be obtained within a relatively short time, said foam having homogeneous cell structure and a good mechanical strength. This was not the case with Examples 5 and 6. As a matter of fact, in Example 5 the foam rise was very slow, while this foam practically collapsed. Moreover, at the end of the reaction, some shrinkage was found. With regard to Example 6, no reaction was seen after a 2-minute contact of ingredients.

In Examples 7 to 13, wherein the so-called "one-shot" technique was also applied, another composition was used, which contained as swelling agent, in addition to water also some amount of "Freon". For these Examples, only the kind of catalyst was varied and by way of comparison, in Example 13, a known catalytic combination not forming part of this invention was used.

As for Examples 1 to 4, a good equilibrated development of the reaction formation of polyurethane foam was found. On the contrary, as it was the case with Example 5, the catalyst used in Example 13 did not allow a commercially valuable product to be obtained. Also as for Examples 1 to 4, hydrophile properties of foams such as obtained according to Examples 7 to 12 were very satisfactory.

In Examples 14 to 17, quasi-prepolymer technique was applied. In each of said Examples, prepolymer (x in the preceding Tables) was prepared from 100 parts of CP 3002 and 65 parts of IPDI. This mixture was heated to 80° C. for about 4 hours until final content of NCO groups remained constant. To this prepolymer, thus having terminal NCO groups, an additional amount of polyol and polyisocyanate, as well as water, the surface active agent and the catalyst were added, the whole having then been intimately mixed for about 10 seconds. Then, the homogeneous mixture so obtained was poured into a container wherein creaming was allowed to freely occur. As resulting from the Tables, the reaction development and hydrohile properties of the foam such as obtained justify an industrial application.

Examples 18 to 31 were carried out according to the same technique as Examples 1 to 13, on other mixtures of ingredients. In Examples 18 to 22 and 25 to 31, catalysts according to the invention were used, while as Examples 5, 6 and 13, Examples 23 and 24 relate by way of comparison to use of conventional catalysts which, as it results from the Tables, do not give favourable results. In Example 23, no reaction was seen after 2 minutes wait, while in Example 5, creaming was very slow, a partial collapse occurred and moreover a rather important shrinkage was seen. On the contrary, in Examples 18 to 22 and 25 to 31, good results were obtained from any point of view, namely as well concerning the reaction itself as the final product.

As already mentioned before, the essential object of this invention is to provide a polyurethane foam suitable to be used as absorption material in medical and hygienic field, particularly for dressings, sanitary towels, and swaddling-clothes, due to the fact that said polyurethane foam does not form noxious aromatic-based products by hydrolysis.

This foam may exist as various forms in its different applications, such as slabs cut from a foam block, which have been optionally subjected to an additional treatment in order to form a skin on at least one of the surfaces of these slabs. This skin can be formed through metal heating plates applied against the foam so as to form a so-called "pelletized" foam.

Optionally, also, according to the invention, a particular absorption article can be obtained by moulding, so as to form a foam with integral skin which, by means of use of sufficient water, as swelling agent, remains permeable enough to allow an effective absorption.

Another form is as flakes, possibly enveloped, in a permeable fabric, for example a cellulose-based fabric.

It is to be understood that the invention is not limited to the embodiments described and that many modifications may be brought thereto without departing from the scope of this invention.

We claim:

1. A process for preparing a hydrophile polyurethane foam absorption material for medical and hygienic use comprising reaction of hydrophile polyol, a polyisocyanate wherein NCO groups are not directly bonded to an aromatic ring, a foam stabilizer, a swelling agent and an effective amount of a catalyst, wherein the catalyst consists essentially of:

(A) at least one compound selected from the group consisting of (1) diazabicycloalkenes of the formula:

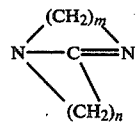

(I)

wherein m varies from 3 to 7 and n from 2 to 4, and salts thereof with organic acids the dissociation constant of which is $Ka \leq 10^{-2}$;

(2) substituted guanidines and salts thereof of the formula:

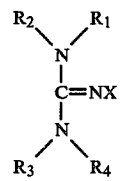

(II)

wherein $R_1$, $R_2$, $R_3$ and $R_4$ can independently represent a $C_1$–$C_4$ alkyl radical, a $C_1$–$C_4$ alkyl radical substituted by a $C_1$–$C_4$ alkoxy radical, or a heterocyclic $C_5$–$C_7$ radical comprising at most two atoms from the group consisting of sulfur and oxygen, $R_1$ and $R_2$ and/or $R_3$ and $R_4$ may form with the adjacent nitrogen a heterocyclic $C_5$–$C_7$ ring containing at most one member from the group consisting of sulfur or oxygen atom, X represents a member selected from the group consisting of hydrogen, phenyl, a phenyl group substituted by one or more $C_1$–$C_4$ alkoxy radicals, $C_1$–$C_{12}$ alkyl radicals or halogens, or represents a radical of the formula:

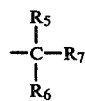

(III)

wherein $R_5$, $R_6$ and $R_7$ can independently represent hydrogen, a $C_1$–$C_4$ alkyl radical or a $C_1$–$C_4$ alkyl radical substituted by a member selected from the group consisting of phenyl, substituted phenyl, $C_1$–$C_4$ alkoxy, $C_6$–$C_{15}$ aryloxy, nitrile or carbalkoxy, or $R_7$ may represent a member selected from the group consisting of a $C_5$–$C_{18}$ alkyl radical, a substituted phenyl radical or a $C_1$–$C_4$ alkoxy radical; or one or two of the groups $R_5$–$R_6$, $R_5$–$R_7$ or $R_6$–$R_7$ can form a cyclic ring of more than one member selected from the group consisting of nitrogen, sulfur or oxygen atom, and X may also represent a radical of the formula:

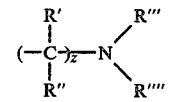

(IV)

wherein z is an integer of from 2 to 12, R' and R" represent a member selected from the group consisting of hydrogen or a $C_1$–$C_4$ alkyl radical, R''' and R'''' represent a member selected from the group consisting of a $C_1$–$C_4$ alkyl radical or form with the adjacent nitrogen of a $C_5$–$C_6$ cycloalkyl radical; and addition salts of said guanidines; and addition salts of guanidines;

(3) substituted biguanidines of the formula:

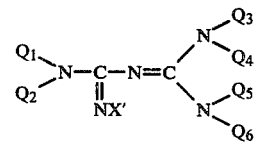

(V)

wherein $Q_1$ to $Q_6$ can independently represent a member selected from the group consisting of $C_1$–$C_4$ alkyl or a $C_3$–$C_4$ cycloalkyl radical, and X' is hydrogen or a carbamoyl radical of the formula:

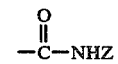

(VI)

in which Z is a monovalent radical remaining after elimination of an isocyanate group from the above mentioned polyisocyanate, $Q_1$ to $Q_6$, X' and Z may optionally be substituted by a member selected from the group consisting of chlorine, bromine or a $C_1$ or $C_2$ alkoxy radical; and (4) substituted biguanidines of the formula:

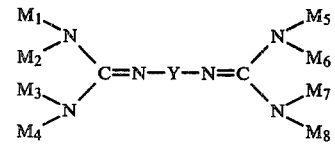

(VII)

wherein $M_1$ to $M_8$ can independently represent a $C_1$–$C_4$ alkyl radical, Y represents a group of the formula:

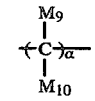

(VIII)

wherein $M_9$ and $M_{10}$ represent a member selected from the group consisting of hydrogen or a $C_1$–$C_4$ alkyl radical, and $\alpha$ is an integer from 3 to 12 or represents a divalent cyclohexyl or a divalent isophorene radical; and (B) at least one alkali or alkaline earth metal salt of an organic acid having a dissociation constant $Ka \leq 10^{-1}$.

2. A process as claimed in claim 1, comprising reaction according to the "one-shot" technique, of a hydrophile polyol, a polyisocyanate wherein NCO groups are not directly bonded to an aromatic ring, a foam stabilizer, a swelling agent and said catalyst.

* * * * *